(12) United States Patent
Kyrölä et al.

(10) Patent No.: US 12,018,988 B2
(45) Date of Patent: Jun. 25, 2024

(54) MEASURING CLIMATE INSIDE A LONGITUDINAL CAVITY OF A STRUCTURE

(71) Applicant: MeshWorks Wireless Oy, Tampere (FI)

(72) Inventors: Marko Kyrölä, Tampere (FI); Timo Remes, Tampere (FI); Ilkka Reis, Tampere (FI); Samuel Niemi, Tampere (FI); Arto Kuivanen, Tampere (FI); Antti Viitanen, Tampere (FI); Joonas Gustafsson, Tampere (FI); Juha Simola, Tampere (FI)

(73) Assignee: MeshWorks Wireless Oy, Tampere (FI)

( * ) Notice: Subject to any disclaimer, the term of this patent is extended or adjusted under 35 U.S.C. 154(b) by 370 days.

(21) Appl. No.: 17/366,701

(22) Filed: Jul. 2, 2021

(65) Prior Publication Data

US 2022/0003612 A1 Jan. 6, 2022

(30) Foreign Application Priority Data

Jul. 3, 2020 (FI) .................................... 20205722

(51) Int. Cl.
*G01K 1/14* (2021.01)
*G01D 11/24* (2006.01)
(Continued)

(52) U.S. Cl.
CPC ............... *G01K 1/14* (2013.01); *G01D 11/24* (2013.01); *G01D 11/245* (2013.01); *G01K 1/024* (2013.01); *G01N 33/00* (2013.01); *G01N 33/383* (2013.01)

(58) Field of Classification Search
CPC .......... G01K 1/14; G01K 1/024; G01D 11/24; G01D 11/245; G01N 33/00; G01N 33/383
(Continued)

(56) References Cited

U.S. PATENT DOCUMENTS

| 2008/0184827 A1* | 8/2008 | Susfalk ................. G01D 9/005 73/866.5 |
| 2009/0100926 A1* | 4/2009 | Kanare ................ G01N 1/2273 73/335.02 |

(Continued)

FOREIGN PATENT DOCUMENTS

| WO | 2004/102187 A1 | 11/2004 |
| WO | 2013030430 A1 | 3/2013 |

(Continued)

OTHER PUBLICATIONS

Office Action issued by the Finnish Patent and Registration Office in Application No. 20205722 dated Oct. 14, 2020. 10 pages.
(Continued)

*Primary Examiner* — Nathaniel T Woodward
(74) *Attorney, Agent, or Firm* — Meunier Carlin & Curfman LLC

(57) ABSTRACT

The invention relates to measuring climate inside a longitudinal cavity of a structure from two or more positions. The cavity has two ends that may be ends open to a surface of the structure, or closed ends inside the structure, or a building comprising the structure. The climate is measured by an arrangement inserted to the cavity. The arrangement comprises plurality of interconnectable sections. The sections comprise at least one sensor section and one or more extension sections. The at least one sensor section and one or more extension sections are interconnectable in a series for insertion inside the cavity. The at least one sensor section is configured to measure at least one quantity indicating the climate. The one or more extension sections are configured to position the at least one sensor section from at least one of the ends of the cavity to a measurement position within the cavity.

3 Claims, 4 Drawing Sheets

(51) Int. Cl.
*G01K 1/024* (2021.01)
*G01N 33/00* (2006.01)
*G01N 33/38* (2006.01)

(58) Field of Classification Search
USPC .......................................................... 73/866.5
See application file for complete search history.

(56) References Cited

U.S. PATENT DOCUMENTS

2014/0260570 A1* 9/2014 Ranwell ............... G01N 33/383
73/73
2017/0366877 A1* 12/2017 Basheer .................... G06F 1/26

FOREIGN PATENT DOCUMENTS

| WO | 2015/038991 A1 | 3/2015 |
| WO | 2019/066655 A1 | 4/2019 |

OTHER PUBLICATIONS

European Search Report of EP 21183361, dated Nov. 16, 2021, 2 pages.

* cited by examiner

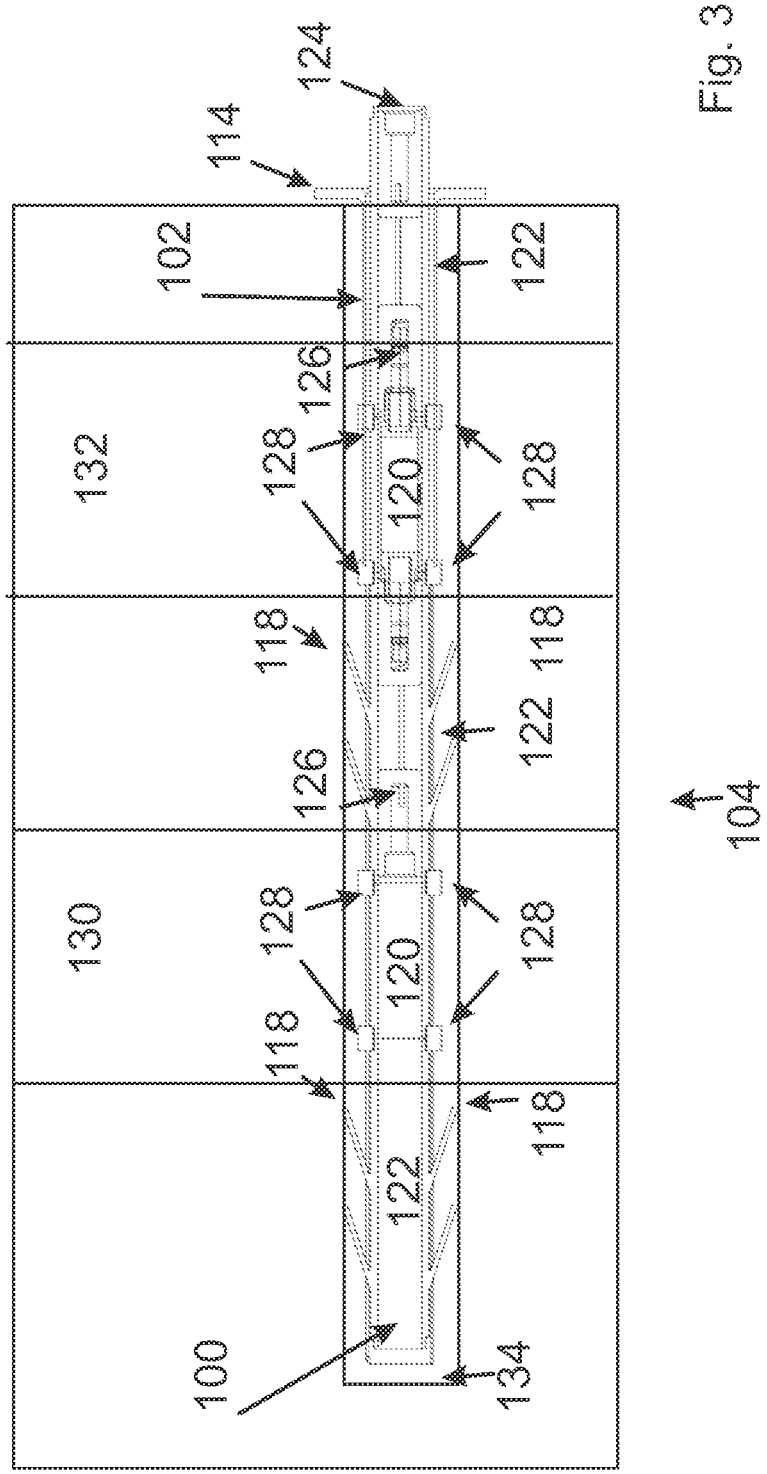

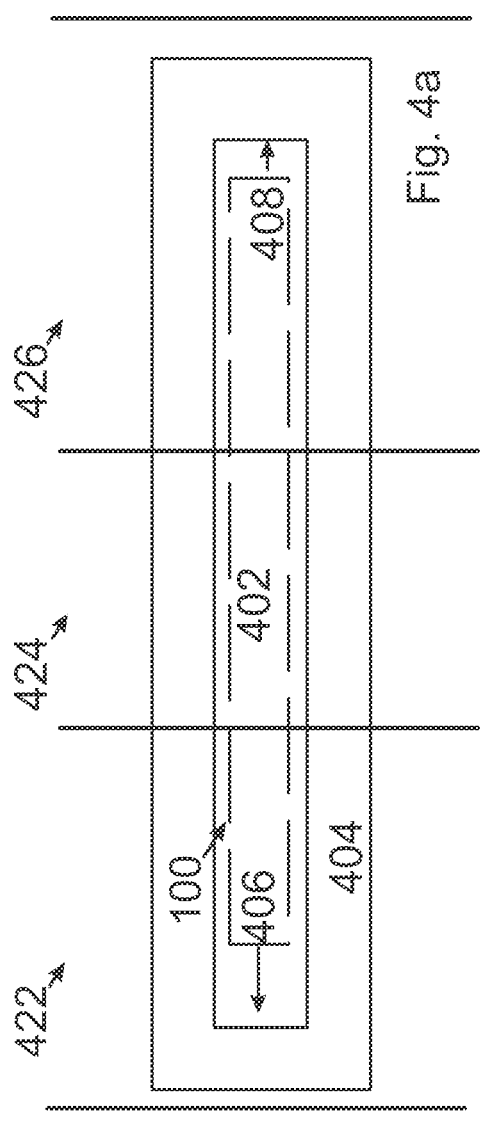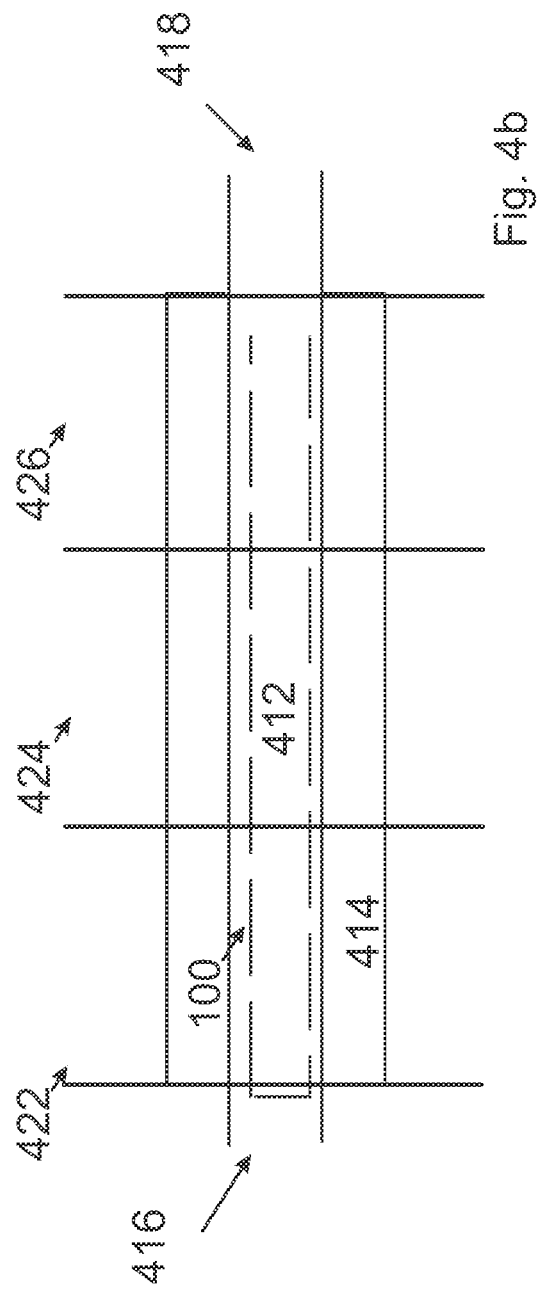

MEASURING CLIMATE INSIDE A LONGITUDINAL CAVITY OF A STRUCTURE

PRIORITY

This application claims priority to Finnish patent application number 20205722 filed on Jul. 3, 2020, the content of which is incorporated herein by reference.

TECHNICAL FIELD

The present invention relates to measuring climate inside a longitudinal cavity of a structure.

BACKGROUND

This section is intended to provide a background or context to the invention that is recited in the claims. The description herein may include concepts that could be pursued but are not necessarily ones that have been previously conceived or pursued. Therefore, unless otherwise indicated herein, what is described in this section is not prior art to the description and claims in this application and is not admitted to be prior art by inclusion in this section.

WO2004102187A1 discloses an apparatus for use in measuring moisture content in concrete. A tube has regions that have reduced wall thickness. Puncturing out the weakened regions of the tube provides selecting the depth at which humidity may enter the tube. A humidity probe may be inserted within the tube to sense the humidity within the tube. Therefore, the humidity probe cannot be brought at the measurement depth and the humidity measurement relies on communication of humidity between the punctured hole and the humidity probe. Therefore, blocking of the punctured hole or direction of the hole being away from a humid area can limit the sensitivity of the humidity measurement.

SUMMARY

The scope of protection sought for various embodiments of the invention is set out by the independent claims. The embodiments, examples and features, if any, described in this specification that do not fall under the scope of the independent claims are to be interpreted as examples useful for understanding various embodiments of the invention.

According to some aspects, there is provided the subject matter of the independent claims. Some further aspects are defined in the dependent claims. The embodiments that do not fall under the scope of the claims are to be interpreted as examples useful for understanding the disclosure.

According to a first aspect there is provided an arrangement for measuring climate inside a longitudinal cavity of a structure, wherein the longitudinal cavity extends between a first end of the longitudinal cavity and a second end of the longitudinal cavity, wherein the arrangement comprises:
  a plurality of interconnectable sections wherein the interconnectable sections comprise
    at least one sensor section and one or more extension sections, wherein the at least one sensor section and one or more extension sections are interconnectable in a series for insertion inside the longitudinal cavity; and
  the at least one sensor section is configured to measure at least one quantity indicating the climate; and
  the one or more extension sections are configured to position the at least one sensor section from at least one of the second end of the longitudinal cavity and the first end of the longitudinal cavity to a measurement position within the longitudinal cavity, wherein the measurement position is one of at least two separate positions within the longitudinal cavity in a longitudinal direction of the longitudinal cavity, when the one or more extension sections and the at least one sensor section are interconnected and the arrangement is inserted inside the longitudinal cavity.

According to a second aspect there is provided an applicator for introducing an arrangement inside a longitudinal cavity of a structure via an open end of the longitudinal cavity, wherein the longitudinal cavity extends between the open end of the longitudinal cavity on a surface of the structure and a closed end of the longitudinal cavity inside the structure, the applicator comprising:
  a longitudinal body having openings at both ends of the body, and
  a passage connecting the openings,
  wherein at least one of the ends has a limiter for limiting an insertion depth of the applicator into the longitudinal cavity, and the applicator is configured to
  receive the arrangement comprising interconnected sections comprising at least one sensor section and one or more extension sections, wherein the at least one sensor section and one or more extension sections are interconnectable in a series for insertion within the applicator inside the longitudinal cavity via the open end of the longitudinal cavity, and the at least one sensor section is configured to measure at least one quantity indicating climate inside the structure, and the one or more extension sections are configured to position the at least one sensor section from at least one of the longitudinally separate ends of the applicator to an insertion position within the applicator, wherein the insertion position corresponds with a measurement position of at least two separate positions within the longitudinal cavity in a longitudinal direction of the longitudinal cavity, when the one or more extension sections and the at least one sensor section are interconnected and the arrangement is inserted inside the applicator and the longitudinal cavity.

According to a third aspect there is provided a kit comprising an arrangement according to an aspect and an applicator for introducing the arrangement inside the longitudinal cavity.

BRIEF DESCRIPTION OF THE DRAWINGS

FIG. 3 illustrates cross-sections of a structure, an arrangement and applicator in accordance with at least some embodiments; and FIGS. 4a and 4b illustrates examples of longitudinal cavities inside a structure in accordance with at least some embodiments.

DETAILED DESCRIPTION

Figure 1:
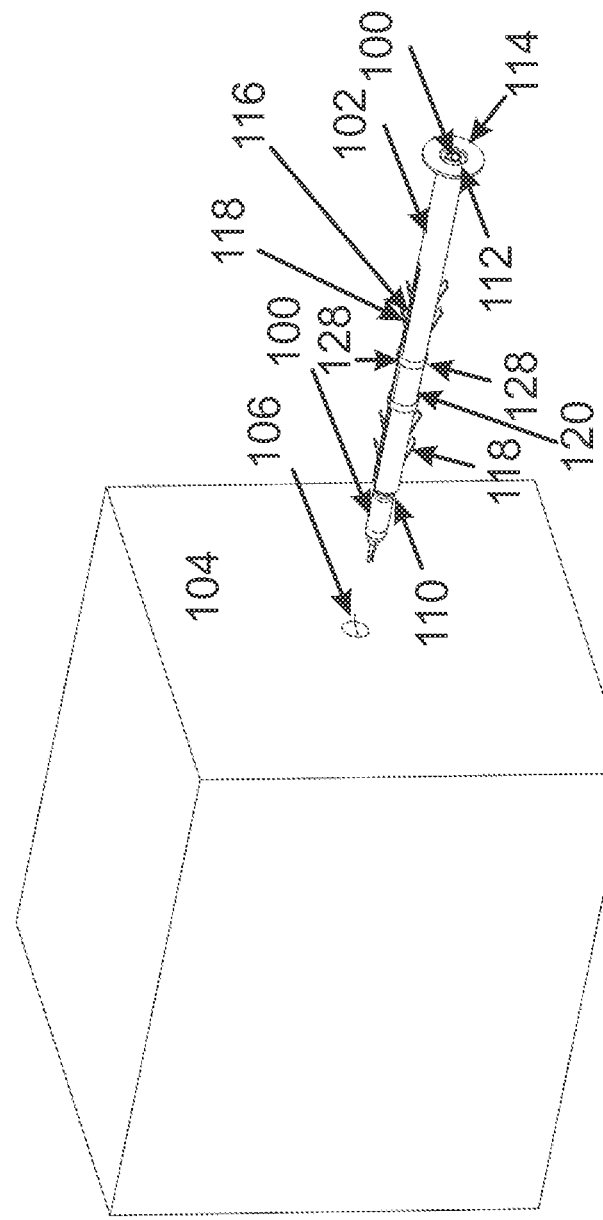
FIG. 1 and FIG. 2 illustrate examples of introducing an arrangement inside a longitudinal cavity of a structure in accordance with at least some embodiments.

There is provided measuring climate inside a longitudinal cavity of structure from two or more measurement positions within the longitudinal cavity. The longitudinal cavity has two ends that may be open ends that are open to a surface of the structure or closed ends inside the structure or a budding comprising the structure. The climate is measured by an arrangement that is inserted to the longitudinal cavity e.g. via the open end or a side of the longitudinal cavity. The arrangement comprises a plurality of interconnectable sections. The sections comprise at least one sensor section and one or more extension sections, wherein the at least one sensor section and one or more extension sections are interconnectable in a series for insertion inside the longitudinal cavity e.g. via the open end of the longitudinal cavity or a side of the longitudinal cavity. The at least one sensor section is configured to measure at least one quantity indicating the climate. The one or more extension sections are configured to position the at least one sensor section from at least one of the ends of the longitudinal cavity, e.g. the closed end and the open end of the longitudinal cavity, to a measurement position within the longitudinal cavity, wherein the measurement position is one of at least two separate positions within the longitudinal cavity in a longitudinal direction of the longitudinal cavity, when the one or more extension sections and the at least one sensor section are interconnected and the arrangement is inserted inside the longitudinal cavity. The number of sensor sections and extension sections may be selected according to properties, e.g., length, of the longitudinal cavity and a number of measurement positions needed inside the longitudinal cavity. In an example, the arrangement may comprise two or more sensor sections and one or more extension sections. When the one or more sensor sections and one or more extensions are ordered and interconnected into a series, the sensor sections are positioned with respect to the extension sections such that the sensor sections may be positioned at least two separate measurement positions inside the within the longitudinal cavity. If only one sensor section is used in the arrangement the arrangement may comprise one or more extensions sections that position the sensor section to a measurement position inside the longitudinal cavity. However, having two or more extensions allows the arrangement to position the sensor section to one of at least two measurement positions. On the other hand, if two or more sensor sections are interconnected with at least one extension section, the sensor sections and extension sections may be ordered to support positioning of the sensor sections to at least three measurement positions inside the longitudinal cavity. At least one of the sensor sections and the extension sections may be provided in different lengths for adapting the sensor sections to measurement positions within the longitudinal cavity, when the sections are interconnected, and the arrangement is positioned within the cavity. For example, at least one sensor section of the arrangement may have a different length than at least a part of the extension sections, or the one or more extensions sections comprise extensions sections of different lengths. The different lengths of the sensor sections and the extension sections provide that the arrangement may be adapted for measuring the climate at various measurement positions inside the longitudinal cavity, Therefore, the arrangement is capable of measuring the climate for different structures, where also measurement positions may be different, e.g., because of different thicknesses and arrangements of layers inside the structure.

An applicator is further provided for introducing an arrangement according one or more example described herein inside a longitudinal cavity of a structure via an open end of the longitudinal cavity. The arrangement and applicator may be provided as a kit that comprises the arrangement and the applicator as described in one or more examples herein. In an example, the kit may comprise different lengths of extension sections and/or different lengths of sensor sections, whereby the arrangement may support positioning the sensor sections to various measurements positions and adaptation of the arrangement for different structures, e.g., thicknesses of layers of the structure. In an example the kit comprises two or more sensor sections that are of at least two different lengths. In an example the kit comprises two or more extension sections that are of at least two different lengths. In an example, the kit comprises sensor sections that are of at least one length and extension sections that are of at least another length that is different from the at least one length of the sensor sections.

Therefore, the various examples described herein may be applied for arrangement, applicator and kit for monitoring climate inside structures and parts of structures in the field of construction engineering. Examples of the structures comprise at least a building, a part of a building, a wall, a ceiling structure and a floor structure.

Figure 2:
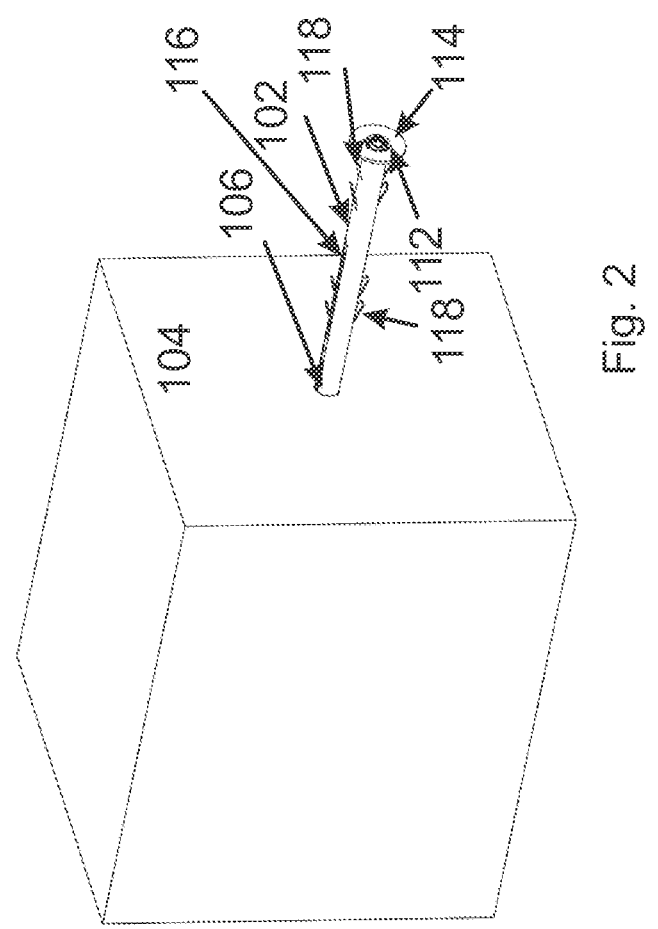

In the following examples are described with reference to features illustrated in FIG. 1, FIG. 2, FIG. 3, FIG. 4a and FIG. 4b. FIG. 1 and FIG. 2 illustrate examples of introducing an arrangement inside a longitudinal cavity of a structure in accordance with at least some embodiments. Same or similar features have been referenced by the same reference numerals in the drawings. FIG. 3 illustrates cross-sections of a structure, an arrangement and applicator in accordance with at least some embodiments. FIGS. 4a and 4b illustrates examples of longitudinal cavities inside a structure in accordance with at least some embodiments.

In FIG. 1 the arrangement 100 and an applicator 102 are illustrated outside of the longitudinal cavity 134. The applicator is used to insert the arrangement into the longitudinal cavity. The arrangement may be first brought into the applicator and then the applicator may be used to bring the arrangement inside the applicator into the longitudinal cavity. FIG. 2 illustrates an example situation, where the applicator 102 has been inserted partially inside the longitudinal cavity. The arrangement 100 provides measuring climate inside a longitudinal cavity of a structure. The climate measurement provides monitoring prevailing conditions within the structure. Monitoring the prevailing conditions provides that conditions within the structure that could negatively affect a health of the structure, a health of people located within a building comprising the structure and energy consumption of the building comprising the structure may be detected. The climate measurements may be carried out in various ways based on one or more measurement technologies. The climate measurements may be based on capacitive, resistive and/or inductive measurements of quantities indicating the climate. Examples of the quantities comprise at least humidity and/or temperature. The climate measurements may be performed by one or more sensors that are brought into the longitudinal cavity, where the sensors may be in contact to a surface of the structure inside the longitudinal cavity or at least close to the surface of the structure inside the longitudinal cavity.

In an example in accordance with at least some embodiments, the arrangement 100 provides measuring humidity and/or temperature within the structure. The arrangement, e.g., the one or more of the extension sections and/or one or more of the sensor sections, may comprise one or more sensors that are configured to measure one or more quantities indicating the climate. The humidity and/or temperature may indicate prevailing conditions that may negatively affect at least a health of the structure. Accordingly, the sensors may comprise at least humidity and/or temperature sensors. For example, humidity within the structure may cause degradation of at least part of the structure which could affect strength of the structure. Alternatively, or additionally, humidity within the structure may cause build-up of mold within the structure which could cause health issues to people who are located within a budding comprising the structure. For example, temperature within the structure may indicate isolation properties of the structure. Monitoring the temperature over a long period of time may indicate changes in the isolation properties. For example, temperature within the structure may be used to determine to increase or decrease heating in a budding comprising the structure, whereby energy consumption of the building may be optimized. For example, temperature within the structure may indicate conditions that are suitable for build-up of mold. Measuring both temperature and humidity may provide accurate information of build-up of mold.

In an example the one or more sensors comprise at least one of a humidity sensor and a temperature sensor.

Referring to FIG. 1, the arrangement 100 has been inserted into an applicator 102 for bringing the arrangement inside the structure by the applicator, and the arrangement and applicator are illustrated outside the structure. The structure 104 has a longitudinal cavity 134 that has an open end 106 on a surface, e.g. an outer surface, of the structure and a closed end inside the structure. The arrangement may be inserted inside the longitudinal cavity by manually pushing the applicator including the arrangement into the longitudinal cavity via the open end.

Examples of the structures 104 comprise structures of buildings such as walls. The structures may have more than one layer, e.g., two, three, four or more layers. The layers may have differences at least in terms of materials. It should be appreciated that the structure may have one or more layers that are the same or similar. Examples of the materials comprise, concrete, concrete blocks, wood and insulation. The layers may be separated within the structure by sections of air, thin films of material and/or thin sheets of material.

The longitudinal cavity 134 extends from the open end 106 in a depth direction of the structure between an open end 106 of the longitudinal cavity on a surface, e.g., outer surface, of the structure and a closed end of the longitudinal cavity inside the structure. Length and diameter of the longitudinal cavity is dimensioned to allow inserting substantially the whole arrangement and the applicator within the longitudinal cavity. In an example, the longitudinal cavity may be drilled to the structure, or the longitudinal cavity may be formed in the structure during manufacturing. Accordingly, the depth of the longitudinal cavity 134 may be determined on the basis of a drilling depth, a length of the applicator and/or a length of the number of, e.g., at least two, interconnected sections of the arrangement.

However, it should be appreciated that a part of the applicator 102 and/or the arrangement 100 may be left outside of the longitudinal cavity, which may affect dimensioning of the longitudinal cavity. In an example, the applicator may comprise a limiter 114 that may be configured to extend in a direction of a surface of the structure, e.g., parallel to the surface of the structure, for limiting an insertion depth of the applicator into the longitudinal cavity. In an example, the arrangement may comprise a data reader interface 124 that may be left outside of the longitudinal cavity for reading data.

In accordance with at least some embodiments, the arrangement comprises a plurality of interconnectable sections 120, 122 wherein the interconnectable sections comprise one or more sensor 120 sections and one or more extension sections 122, wherein the one or more sensor sections and one or more extension sections are interconnectable in a series for insertion inside the longitudinal cavity 134 via the open end of the longitudinal cavity. The one or more sensor 120 sections may comprise at least one sensor section that is configured to measure at least one quantity indicating the climate. The one or more extension sections are configured to position the one or more sensor 120 sections from at least one of the closed end of the longitudinal cavity and the open end of the longitudinal cavity to at least one measurement position 130, 132 within the longitudinal cavity, wherein the measurement position is one of at least two separate positions within the longitudinal cavity in a longitudinal direction of the longitudinal cavity, when the one or more extension sections and the at least one sensor section are interconnected and the arrangement is inserted inside the longitudinal cavity.

In an example, the one or more extension sections 122 may be provided in different lengths for positioning the at least one sensor sections 120 to the measurement position within the longitudinal cavity, when the sections are interconnected and the arrangement is positioned within the cavity. It should be appreciated that when there are more extension sections than needed for the arrangement considering the positioning of the sensor section and/or the length of the cavity, the extra extension sections may be left out of the longitudinal cavity and not interconnected with the at least one sensor section. Moreover, it should be appreciated that one or more of the extension sections may be configured to serve for a sensor section, whereby in practice a sensor section may be used for positioning another sensor section to a measurement position 130, 132. However, if the longitudinal cavity has two or more measurement positions, sensor sections and/or extension sections serving for sensor sections may position each other to the measurement positions.

It should be appreciated that extensions sections 122 in accordance to at least some embodiments may have different lengths. For example, one or more extension sections to be interconnected with at least one sensor 120 section when positioned within a longitudinal cavity may be selected from at least two extension sections that have different lengths. In this way the extension sections may be selected based on their length such that the at least one sensor section is positioned at a measurement position 130, 132 inside the longitudinal cavity, when the sections are interconnected, and the arrangement is positioned inside the longitudinal cavity.

In an example the interconnectable sections 120, 122 may comprise connecting surfaces at longitudinally separate ends of the bodies of the sections for electrically and mechanically coupling the sections, as will be described in more detail below.

In an example in accordance with at least some embodiments, at least part of the one or more extension sections 122 are configured to serve for a sensor section 120. In this way the extension sections may measure one or more quantities indicating the climate inside the structure. In an example an extension section may be configured to measure at least one quantity indicating the climate similar to the sensor sections. The extension sections 122 may comprise sensors for measuring the one or more quantities indicating the climate. In an example, the one or more extension sections 122 may comprise extension sections of different lengths, whereby the at least sensor section 120 may be interconnected with selected ones of the one or more extension sections that position the at least one sensor section at the measurement position 130, 132, when the selected extensions sections are interconnected with the at least one sensor section and the interconnected sections are inserted within the cavity. The extension sections may be selected based on the length of interconnected selected one or more extension sections and the at least one sensors section substantially matching the depth of the longitudinal cavity.

In an example, the one or more extension sections 122 and the at least one sensor section 120 may be interconnected in a series, whereby the order of the sections may be determined on the basis of the position of one or more measurement positions within the longitudinal cavity 134. Accordingly, the sections may be ordered with respect to one another such that the at least one sensor section is positioned at a measurement position, when the arrangement is within the longitudinal cavity.

In accordance with at least some embodiments, the applicator 102 comprises a longitudinal body having openings 110, 112 at both ends of the body, and a passage connecting the openings, wherein at least one of the ends has a limiter 114 for limiting an insertion depth of the applicator into the cavity, and the applicator is configured to receive the arrangement comprising interconnected sections comprising at least one sensor section and one or more extension sections, wherein the at least one sensor section and one or more extension sections are interconnectable in a series for insertion within the applicator inside the longitudinal cavity via the open end 106 of the longitudinal cavity, and the at least one sensor section is configured to measure at least one quantity indicating climate within the structure, and the one or more extension sections are configured to position the at least one sensor section from at least one of the longitudinally separate ends of the applicator 102 to an insertion position within the applicator, wherein the insertion position corresponds with a measurement position 130, 132 of at least two separate positions within the longitudinal cavity in a longitudinal direction of the longitudinal cavity, when the one or more extension sections and the at least one sensor section are interconnected and the arrangement is inserted inside the applicator and the longitudinal cavity.

The measurement position 130, 132 may be a position within the longitudinal cavity that is in a depth direction of the longitudinal cavity at an area of a layer of the structure. The area may be defined by a depth of the layer and the position of the layer within the structure, e.g., from the open end 106 of the longitudinal cavity. The structure may have more than one layer, whereby each layer may be measured by the arrangement comprising sensor sections that are interconnected into series to be inserted into the longitudinal cavity 134 at the depth of the layers, whereby at least one sensor section is positioned at a measurement position located at a depth of each layer of the structure. The depth of the layer within the structure may be a range of positions within the structure which may be defined based on a thickness of the layer.

In an example the limiter 114 is a flange that is configured to extend on the surface of the structure. In this way the limiter may prevent insertion of the applicator 102 too deep into the longitudinal cavity 134. Inserting the applicator too deep could prevent removal of the applicator.

In an example in accordance with at least some embodiments, the applicator 102 comprises one or more slots 116 for allowing impediments 118 of the arrangement inside the applicator to engage walls of the cavity for maintaining the arrangement introduced inside the cavity, when the applicator is removed from the cavity. The slots may extend in a longitudinal direction of the applicator. The impediments may resist removal of the arrangement while the slots provide that the applicator may be moved away from the closed end of the cavity. In this way the position of the arrangement and measurement positions of the sensor sections may be maintained while removal of the applicator is provided.

In an example the arrangement may comprise impediments 118 on opposite sides of the arrangement. Herein the opposite sides refer to opposite sides in a transverse direction to the longitudinal direction of the arrangement. Accordingly, the impediments may extend in a perpendicular direction to a direction of length of the arrangement and the applicator 102. In this way, the impediments provide even support for the arrangement positioned within the cavity. In an example, positions of the slots on the applicator provide that the impediments may extend out of the applicator, when the arrangement is within the applicator.

In an example, the passage of the applicator 102 may comprise a solid section without slots. The solid section may extend from the limiter 114 at one end of the applicator towards the opposite end of the applicator and up to a length of the passage between the limiter and the opposite end of the applicator. The slots may extend from the solid section all the way to the end of the applicator opposite to the end of the applicator comprising the limiter. In this way the passage may be split from end of the applicator opposite towards the end of the applicator comprising the limiter up to the solid section of the applicator. The slots provide that the impediments of the arrangement inside the applicator may extend out of the passage in the transverse direction to the length of the applicator and the arrangement may be maintained at its position by the impediments engaging the cavity wads surrounding the applicator. Since the slots extend to the end of the applicator opposite to the limiter, effectively partially splitting the passage in the direction perpendicular to the length direction of the applicator, the slots provide that the applicator may be pulled out of the longitudinal cavity 134, leaving the arrangement at its position within the longitudinal cavity.

In an example in accordance with at least some embodiments, the at least one sensor section 120 and the one or more extension sections 122 comprise data transfer parts 126 and a data reader interface 124 for forming a data transfer connection between the data reader interface and the at least one sensor section for measuring the at least one quantity indicating the climate by the at least one sensor section via the data reader interface, when the one or more extension sections and the at least one sensor section are interconnected. The data reader interface provides that climate measurements performed by the at least one sensor section may be transferred from the at least one sensor section to a climate measurement device located outside of the cavity. Examples of the climate measurement device comprise a computer, data communications device or a wireless communications module that may comprise computer program code or instructions that when executed cause performing one or more climate measurements by the arrangement and receiving data indicating the climate. The data indicating the climate indicates a climate measured by a specific sensor section, whereby the climate at the measurement position 130, 132 of the sensor section may be determined.

In an example the extension sections 122 and the sensor sections 120 comprise data transfer parts 126 and connectors of the data transfer parts are provided at longitudinally separate ends of the longitudinal bodies of the sensor sections and the extension sections. When the extension sections and the sensor sections are interconnected in a series, the connectors of the data transfer parts are connected for data transfer between the sections. One of the extension sections may comprise a data reader interface 124 for reading the climate measurements from the sensor sections. It should be noted that a separate data reader interface may not be necessary but depending on the data transfer parts, the connectors of the data transfer parts at the ends of the sections may serve for a data reader interface, whereby a connector at the end of an extension section or a sensor section that is closest to the open end 106 may serve for a data reader interface.

It should be noted that the data transfer parts 126 and the data reader interface 124 provide a data transfer connection between sensor sections of the arrangement and a device located outside of the longitudinal cavity 134. The data transfer connection may be a wireless connection, wired connection or a data transfer bus that connects the sensor sections of the arrangement to the data reader interface.

It should be noted that the data reader interface 124 may be provided by an extension section 122. In an example, the extension section may comprise the data reader interface at one end of a longitudinal body of the extension section.

In an example in accordance with at least some embodiments the at least one sensor section 120 is addressable via the data reader interface 124 and the data transfer parts 126, and configured, in response to the at least one sensor section receiving a message addressed to the at least sensor section, from the interface, to send data indicating one or more values of the at least one quantity indicating the climate.

In an example in accordance with at least some embodiments the data reader interface 124 comprises a connector for a wired connection to a data communications device, or the data reader 124 interface comprises connector for a wireless communications module.

In an example in accordance with at least some embodiments, the arrangement 100 is configured to removably connect to the wireless communications module and the wireless communications module comprises a battery, and the arrangement is configured to galvanically connect the battery to the data transfer parts 126, when the wireless communications module is connected to the arrangement. In this way the arrangement may be first inserted within the longitudinal cavity 134 and the wireless communications module may be connected to the arrangement afterwards or disconnected for servicing. In an example the wireless communications module may be connected to a data reader interface 124 at the arrangement. The battery provides feeding electricity to the data transfer parts, whereby the at least one sensor section may be powered through the data transfer parts. Accordingly, the data transfer parts may serve for transfer of climate measurement data and additionally also for power transfer.

It should be noted that power may be supplied to sensor sections for performing climate measurements within the longitudinal cavity in many ways; either power is conducted with wires along with the measurement control signaling, or one or more of the interconnected sensor sections may be equipped with a battery placed inside the cavity, or the sensor section get their power via a wireless charging-type interface whose energy source is outside the measurement arrangement inside the cavity.

In an example in accordance with at least some embodiments, the arrangement 100 comprises a plurality of sensor sections that are independently addressable via the data reader interface 124 for reading data indicating one or more values of the at least one quantity indicating the climate from each of the sensor sections connected to the data reader interface by the data transfer parts 126.

In an example in accordance with at least some embodiments the one or more extension sections 122 and the at least one sensor section 120 are configured to position the data reader interface at the open end of the longitudinal cavity 134, when the one or more extension sections and the at least one sensor section are interconnected and the arrangement is inserted inside the longitudinal cavity. In an example, the one or more extension sections 122 and the at least one sensor section 120 are interconnectable and the one or more extensions comprise impediments 118 for engaging walls of the longitudinal cavity, when the arrangement is inside the longitudinal cavity. In an example, the lengths of the one or more extension sections and the at least one sensor section may be dimensioned to support positioning the data reader interface at the open end of the longitudinal cavity. The extension sections may comprise extension sections of different lengths, e.g. at least two different lengths or more than two different lengths such as three or four different lengths, whereby the at least one sensor section may be interconnected with selected ones of the one or more extension sections for positioning the data reader interface at the open end of the longitudinal cavity, when the selected extensions sections are interconnected with the at least one sensor section and the interconnected sections are inserted within the cavity. The extension sections may be selected based on the length of interconnected selected one or more extension sections and the at least one sensors section substantially matching the depth of the longitudinal cavity or at least positioning the sensor sections of the arrangement to measurement positions.

In an example in accordance with at least some embodiments at least part of the at least one sensor section 120 and the one or more extension sections 122 comprise impediments 118 for resisting removal of the arrangement through the open end, when the one or more extension sections and the at least one sensor section are interconnected and the arrangement is inserted inside the longitudinal cavity 134.

In an example the impediments 118 are arranged on one or more of the extension sections 122. The impediments may release material from cavity walls, when the impediments engage the cavity walls. Therefore, the released material could affect the climate measurements if the impediments were arranged on the sensor section, whereby the impediments are preferred on the extension sections.

In an example in accordance with at least some embodiments the at least one sensor section 120 and the one or more extension sections 122 comprise sealings 128 for sealing the at least one sensor section within a portion of the longitudinal cavity 134. The sealings provide that the climate measurement may be performed by the sensor section within an isolated space inside the longitudinal cavity. The sealings prevent transfer of gases between the isolated space and other parts of the longitudinal cavity, whereby accuracy of the climate measurement is supported. In an example, when the sensor section is configured to measure humidity, the isolated space cannot dry through air transfer via the longitudinal cavity and/or humidity cannot transfer between different sensors sections inserted into the longitudinal cavity.

In an example the sealings 128 may be arranged on the at least one sensor section.

In an example in accordance with at least some embodiments the sealings 128 are compressible in a direction perpendicular to the longitudinal direction of the longitudinal cavity 134 for facilitating insertion of the arrangement inside the longitudinal cavity. The compressible property of the sealings may be provided by a compressible material of the sealings.

In an example, the sealings 128 may be compressed against an applicator 102, when the arrangement is inside the applicator. Then, when the arrangement 100 has been brought inside the applicator inside the longitudinal cavity 134, the applicator may be moved and the sealings 128 may expand to seal the at least one sensor section such that the sensor section may perform measurements of the at least one quantity indicating the climate within a portion of the longitudinal cavity. The expandable property of the sealings may be provided by an expandable material of the sealings. Therefore, the sealings may be compressible and/or expandable. Preferably the sealings are both compressible and expandable. Therefore, the material of the sealings may be both compressible and expandable. The portion of the longitudinal cavity may comprise a specific layer of the structure, whereby the performed climate measurements may indicate at least one quantity indicating the climate for the specific layer of the structure.

In an example in accordance with at least some embodiments, the one or more extension sections 122 and the at least one sensor section 120 comprise
- longitudinal bodies, and
- connecting surfaces at longitudinally separate ends of the bodies, and
- the sealings 128 are provided at at least one of the longitudinally separate ends on outer surfaces of the bodies of the one or more extension sections and the at least one sensor section and the sealings are configured to extend beyond a measure of the outer surfaces in the longitudinal direction of the bodies for sealing the connecting surfaces of the interconnected sections.

In an example, the connecting surfaces of the sections 120, 122, may be configured to connect sections with each other. Accordingly, a connecting surface of an extension section may be configured to connect with a connecting surface of a sensor section and a connecting surface of another extension section. Similarly, a connecting surface of a sensor section may be configured to connect with a connecting surface of an extension section sensor section and a connecting surface of another sensor section. The connecting surfaces at both ends of the bodies may be the same.

In an example, the connecting surfaces of the sections 120, 122 may be configured to connect the sections by way of mechanical and electrical coupling. The mechanical coupling provides that the sections are maintained connected when the arrangement is being inserted into the longitudinal cavity and when the arrangement is positioned within the longitudinal cavity. The mechanical coupling may be implemented by threading of the connecting surfaces and/or a press-fit connection. In the press-fit connection connecting surfaces are fitted tightly to one another, e.g., by one of the coupled connecting surfaces being a male connector and the other a female connector. Together with threading of the connecting surfaces, the connecting parts may be brought in contact and even partially inserted into one another. Then, when the contacting surfaces and corresponding sections are rotated with respect to one another, the coupling may be caused by the threading of the connecting surfaces. Additionally, a locking mechanism may be provided to lock the threading of the connecting surfaces that are rotated sufficiently. The electrical coupling provides that data transfer parts 126 of the sections may be connected for data transfer and power transfer for the sensor sections 120.

It should be appreciated that the sealings 128 may be provided on both ends of the sensor section 120, whereby the sealings may be omitted from the extension sections 122 that are connected to the sensor section. On the other hand, the sealings may be provided on both ends of the extension section, whereby the sealings may be omitted from the sensor sections that are connected to the extension section. On the other hand, both the sensor section and the extension section may be provided with sealings at both ends and configured to form a sealed connection when the sections are interconnected. On the other hand, both the sensor section and the extension section may be provided with sealings at both ends and the sealings may be removed from one of the interconnectable sections for interconnecting the sections. On the other hand, the sensor section and the extension section may be provided with a sealing on one of their ends, whereby the sections may be interconnected by connecting a sealed end of one section with a non-sealed end of another section, i.e. an end of a section without a sealing. It should be appreciated that a sealing provided on one section may provide a press-fit connection with an end of another section without a sealing. In this way the sealing may be e.g., a sleeve around outer surfaces of the interconnected sections.

FIGS. 4a and 4b illustrates examples of longitudinal cavities inside a structure in accordance with at least some embodiments. FIG. 4a illustrates a longitudinal cavity 402 inside a structure 404. The longitudinal cavity 402 extends between two closed ends 406, 408. In an example the structure 404 may be a block of concrete or a block of other budding material and the longitudinal cavity may be formed to the structure during a manufacturing phase of the structure or during a construction of a building comprising the structure. During manufacturing of the structure or construction of the building, the longitudinal cavity may be open from its side, whereby an arrangement 100 for measuring climate may be positioned inside the longitudinal cavity from the side of the cavity, instead of an open end as discussed in some embodiments herein. After the open side of the longitudinal cavity has been closed during manufacturing of the structure or when the open side is covered by other means, e.g., by another structure during manufacturing of a building, the arrangement is built inside the longitudinal cavity, contact of the arrangement with the environment is limited and the arrangement is not visible outside of the structure. In practice it may be regarded that the arrangement becomes a part of the structure itself. Thanks to the adaptable length of the arrangement and possibilities to position the sensor section at a measurement position, the arrangement may be inserted into longitudinal cavities of various kinds of structures which may have different lengths and one or more measurement positions. The arrangement may comprise a data reader interface for transferring climate measurements performed by one or more sensor sections to a climate measurement device located outside of the cavity. As a difference to at least some embodiments described herein the data reader interface is positioned inside the longitudinal cavity. The data reader interface may be configured for data transfer over a wireless connection, e.g., by a wireless communications module.

FIG. 4b illustrates a longitudinal cavity 412 inside a structure 414. The longitudinal cavity 412 extends between two open ends 416, 418 to the surface of the structure. The open ends provide that the arrangement 100 may be in contact and observed from both sides of the structure, e.g., from inside a building or room or outside a building or room that comprises the structure. Having two open ends provides that once the arrangement has been inserted via one of the open ends, the arrangement may be removed from via both of the open ends. Particularly, when the arrangement has impediments, removal via one of the open ends may be prevented, whereby the other open end may still provide removal of the arrangement without necessarily damaging the arrangement. The arrangement, e.g., the sections of the arrangement, may comprise sealings as needed or separate sealings may be installed to the open ends for supporting measurements of the climate inside of the longitudinal cavity. In an example, a sealing may provide also a surface coating of the structure.

In an example, the longitudinal cavity 402, 412 may be within a wall of a building. The wall may have more than one layer 422, 424, 426 and the longitudinal cavity may extend between two or more layers of the wall. Accordingly, the longitudinal cavity may be inside a structure, e.g., a wall, that is layered. Accordingly, the wall comprises two or more layers. In an example the wall may comprise an outer layer 422, an inner layer 426 and at least one mid-layer 424. The outer layer may form an outer surface of the building for protecting the inside of the building and the mid-layer against environmental conditions. The inner layer may form an inner surface of the building. The inner surface of the building protects the mid-layer from direct contact with the conditions inside the building and supports attaching interior decorations to the wall. The longitudinal cavity may have an open end 416 that provides an opening to outside of the building and/or an open end 418 that provides an opening to inside of the building. The at least one mid-layer provides at least thermal insulation between the environment outside of the building and the environment inside the building. The at least one mid-layer may be made of mineral wool or polyurethane. The outer layer and/or inner layer may be made of one or more of wood, concrete, brick and steel. Since the wall has more than one layer with dedicated functionalities, the structure of the wall may be referred to a sandwich wall. A total thickness of the wall between an outer surface and an inner surface may be e.g., 25 cm, whereby the mid-layer may have a thickness of 15 cm, and the outer layer rand the inner layer may be 5 cm thick each. The layers of the wall may provide measurement positions for the arrangement 100 described herein.

In an example, the arrangement 100 comprises more than one or more sensor sections 120 and one or more extension sections 122 and the one or more extension sections may be configured to position each of the sensor sections to a separate measurement position 130,132. The layers 422,424, 426 of the wall may provide measurement positions for the sensor sections.

In an example, the arrangement 100 for measuring a climate within a longitudinal cavity 402,412 of a wall may have at least one sensor section having a length of 5 to 10 cm, for example about 7 cm such as 7.5 cm, and at least one extension section having a length of 5 to 10 cm.

In an example, the arrangement 100 for measuring a climate within a longitudinal cavity 402, 412 of a wall may comprise one or more sensor sections 120 interconnected in a series with one or one or more extension 122 sections, whereby the one or more sensor sections may be positioned inside the longitudinal cavity 402, 412 at one or more measurement positions 130,132. Therefore, each sensor section may be positioned to a corresponding measurement position. The dimensions, e.g., the lengths, of the extensions sections and the sensor sections may be adapted based on a number of layers and thicknesses of the layers of the structure. For example, when at least one extension section and at least one sensor section are interconnected, the at least one sensor section is positioned at a measurement position inside the longitudinal cavity and the at least extension section may extend between the end of the longitudinal cavity 406, 416 and the at least one sensor section. The at least one extension section may be for example at the open end 416, at the outer surface of the structure. The measurement position may be at a position, e.g., inside, of a layer of the structure. The measurement position may be inside the outer layer 422, inner layer 424 or a mid-layer 426. When more than one sensor sections are interconnected with at least one extension section, each of the sensor sections may be positioned at a measurement position. Accordingly, each of the sensor sections may be inside a different layer of the structure.

Example configurations of the arrangement 100 comprise at least an extension section 122 interconnected with a sensor section 120; an extension section 122 interconnected with a sensor section 120 and another extension section 122; and an extension section interconnected with a sensor section and another sensor section. The lengths of the extension section and sensor sections may be adapted to positions of layers 422, 424, 426 inside a structure, e.g., a wall, such that the sensor sections are inside the layers, when the arrangement is inside a longitudinal cavity 402,412 of the structure. In an example, a length of the extension section 122 may be determined by a distance between an open end 416 of the longitudinal cavity and a next layer inside the structure, e.g., the mid-layer 424, in the depth direction of the structure. In an example, a length of the sensor section 120 interconnected to the extension section may be determined by a thickness of the mid-layer 424. It should be noted that the structure, e.g., a wall, may comprise more than one mid-layer that are arranged one after another in a direction of the thickness of the structure. Accordingly, the structure may comprise an outer mid-layer and an inner mid-layer that is deeper inside the structure than the outer mid-layer that may be closer to the open end 416 or the closed end 406 of the longitudinal cavity than the inner mid-layer. The open end 416 or the closed end 406 may be at the end of the longitudinal cavity closer to an outer surface of the structure than an opposite end 408,418 of the longitudinal cavity. Then, the arrangement for measuring climate inside the outer mid-layer and the inner mid-layer may comprise an extension section 122 having a length determined by a distance between the open end 416 or closed end 406 of the longitudinal cavity and a next layer inside the structure, e.g., the outer mid-layer. Then, a length of the sensor section 120 interconnected directly in series with the extension section may be determined by a thickness of the outer mid-layer. A further sensor section may be interconnected as a next section interconnected in series to the arrangement for measuring climate at a measurement position inside the inner mid-layer. The length of the further sensor section may be determined by a thickness of the inner mid-layer and a total length of the arrangement without the further sensor section. In this way the extension section supports positioning the sensor section interconnected directly to the extension section to a measurement position inside the inner mid-layer and the extension section and the sensor section support positioning the further sensor section inside the inner mid-layer. Using the example dimension 5 cm for the inner layer 422 and the example dimension 15 cm for the mid-layer 424, where each of the outer mid-layer and inner mid-layer may be 15 cm, the extension section extending from the outer surface of the structure inside to the structure may have a length 5 cm based on the dimension of the outer layer and sensor sections interconnected in series to the extension section may each have a length of at most 15 cm, which would allow interconnecting two sensor sections in series to the extension section such that each of the sensor sections is positioned inside one of the inner mid-layer and the outer mid-layer. On the other hand, using a length of 7.5 cm for the sensor sections, the extension section may be directly interconnected to a first sensor section that may be in this way positioned inside the outer mid-layer, when the arrangement is inside the longitudinal cavity 402,412, since a total length of the arrangement becomes 12.5 cm. However, since a distance of 12.5 cm from the outer surface of the structure is inside the outer-mid layer, connecting a further sensor section of 7.5 cm would not provide a reliable measurement of the climate inside the inner mid-layer. Therefore, at least one further extension section may be connected to first sensor section in order to have a total length of the arrangement at 20 cm that is the combined thickness of the outer layer and the outer mid-layer, whereby interconnecting the second sensor section to the arrangement would make a total length of the arrangement into 27.5 cm and position the second sensor section inside the inner mid-layer of the structure. The at least one further extension section may be less than 15 cm in order to keep a total length of the arrangement less than a combined thickness of the outer layer, the outer mid-layer and the inner mid-layer, that is 35 cm. On the other hand, the at least one further extension section may be at least 7.5 cm in order to position the second sensor section interconnected to the at least one further extension section inside the inner mid-layer. Therefore, the at least one further extension may have a length that is less than 15 cm and higher than 7.5 cm, for example 10 cm. On the other hand two extension sections of 5 cm may be interconnected to the first sensor section for positioning the second sensor section inside the inner mid-layer.

In the foregoing description, at least some examples refer to at least one, for example at least one sensor section, and it should be understood that more than one, e.g. a plurality of sensor sections may be used. Accordingly, properties described for one device, e.g. sensor section of extension section may apply also to further sensor sections and extension section. In essence the arrangement in accordance with the examples may be of variable length because the length of the arrangement is defined by the number of interconnected sensor sections and extension sections. Accordingly, in order to measure climate at any measurement position within a longitudinal cavity, a number of sensor sections corresponding to the measurement positions are interconnected by the extension sections and inserted into the longitudinal cavity for measuring the climates at each of the measurement positions.

The foregoing description has provided by way of exemplary and non-limiting examples a full and informative description of the exemplary embodiment of this invention. However, various modifications and adaptations may become apparent to those skilled in the relevant arts in view of the foregoing description, when read in conjunction with the accompanying drawings and the appended claims. However, all such and similar modifications of the teachings of this invention will still fail within the scope of this invention.

The invention claimed is:

1. An applicator for introducing an arrangement inside a longitudinal cavity of a structure via an open end of the longitudinal cavity, wherein the longitudinal cavity extends between the open end of the longitudinal cavity on a surface of the structure and a closed end of the longitudinal cavity inside the structure, the applicator comprising:

a longitudinal body having openings at both ends of the body, and a passage connecting the openings, wherein at least one of the ends has a limiter for limiting an insertion depth of the applicator into the longitudinal cavity, and the applicator is configured to receive the arrangement comprising interconnected sections comprising at least one sensor section and one or more extension sections, wherein the at least one sensor section and one or more extension sections are interconnectable in a series for insertion within the applicator inside the longitudinal cavity via the open end of the longitudinal cavity, and the at least one sensor section is configured to measure at least one quantity indicating climate inside the structure, and the one or more extension sections are configured to position the at least one sensor section from at least one of the longitudinally separate ends of the applicator to an insertion position within the applicator, wherein the insertion position corresponds with a measurement position of at least two separate positions within the longitudinal cavity in a longitudinal direction of the longitudinal cavity, when the one or more extension sections and the at least one sensor section are interconnected and the arrangement is inserted inside the applicator and the longitudinal cavity, and the applicator further comprising one or more slots for allowing impediments of the arrangement inside the applicator to engage walls of the longitudinal cavity for maintaining the arrangement introduced inside the longitudinal cavity, when the applicator is removed from the longitudinal cavity.

2. A kit comprising:

an arrangement for measuring climate inside a longitudinal cavity of a structure, wherein the longitudinal cavity extends between a first end of the longitudinal cavity and a second end of the longitudinal cavity, wherein the arrangement comprises:

a plurality of interconnectable sections wherein the interconnectable sections comprise at least one sensor section and one or more extension sections, wherein the at least one sensor section and one or more extension sections are interconnectable in a series for insertion inside the longitudinal cavity; and the at least one sensor section is configured to measure at least one quantity indicating the climate; and the one or more extension sections are configured to position the at least one sensor section from at least one of the second end of the longitudinal cavity and the first end of the longitudinal cavity to a measurement position within the longitudinal cavity, wherein the measurement position is one of at least two separate positions within the longitudinal cavity in a longitudinal direction of the longitudinal cavity, when the one or more extension sections and the at least one sensor section are interconnected and the arrangement is inserted inside the longitudinal cavity;

the kit further comprising an applicator for introducing the arrangement inside the longitudinal cavity, wherein the applicator provides introducing the arrangement inside the longitudinal cavity of a structure via an open end of the longitudinal cavity, wherein the longitudinal cavity extends between the open end of the longitudinal cavity on a surface of the structure and a closed end of the longitudinal cavity inside the structure, the applicator comprising:

a longitudinal body having openings at both ends of the body, and a passage connecting the openings, wherein at least one of the ends has a limiter for limiting an insertion depth of the applicator into the longitudinal cavity, and the applicator is configured to receive the arrangement comprising interconnected sections comprising at least one sensor section and one or more extension sections, wherein the at least one sensor section and one or more extension sections are interconnectable in a series for insertion within the applicator inside the longitudinal cavity via the open end of the longitudinal cavity, and the at least one sensor section is configured to measure at least one quantity indicating climate inside the structure, and the one or more extension sections are configured to position the at least one sensor section from at least one of the longitudinally separate ends of the applicator to an insertion position within the applicator, wherein the insertion position corresponds with a measurement position of at least two separate positions within the longitudinal cavity in a longitudinal direction of the longitudinal cavity, when the one or more extension sections and the at least one sensor section are interconnected and the arrangement is inserted inside the applicator and the longitudinal cavity; and the applicator comprising one or more slots for allowing impediments of the arrangement inside the applicator to engage walls of the longitudinal cavity for maintaining the arrangement introduced inside the longitudinal cavity, when the applicator is removed from the longitudinal cavity.

3. The kit of claim 2, wherein the at least one sensor section has a different length than at least a part of the extension sections, or the one or more extensions sections comprise extensions sections of different lengths.

* * * * *